United States Patent [19]

Mast

[11] 4,338,294
[45] Jul. 6, 1982

[54] ANTIPERSPIRANT COMPOSITIONS AND METHODS FOR THEIR PREPARATION

[75] Inventor: Rolf Mast, Scottsdale, Ariz.

[73] Assignee: Armour-Dial, Inc., Phoenix, Ariz.

[21] Appl. No.: 641,445

[22] Filed: Dec. 17, 1975

[51] Int. Cl.³ .................. A61K 7/34; A61K 7/36; A61K 7/38

[52] U.S. Cl. ..................... 424/68; 424/357

[58] Field of Search .............. 424/47, 68, 65, 357

[56] References Cited

U.S. PATENT DOCUMENTS

| | | | |
|---|---|---|---|
| 2,571,030 | 10/1951 | Govett et al. | 424/68 X |
| 2,783,181 | 2/1957 | Henkin et al. | 424/68 |
| 2,890,987 | 6/1959 | Hilfer | 424/68 |
| 2,955,983 | 10/1960 | Messina | 424/68 |
| 3,499,961 | 3/1970 | Dobson et al. | 424/68 |
| 3,634,480 | 1/1972 | Sheffield | 424/68 |
| 3,708,435 | 1/1973 | Starkman | 424/357 |
| 3,832,468 | 8/1974 | Hyson et al. | 424/357 |
| 3,929,986 | 12/1975 | Bouillon et al. | 424/68 |

FOREIGN PATENT DOCUMENTS 844769  9/1961  France ................. 424/184

OTHER PUBLICATIONS

Barr American Perfumer and Cosmetics, 2/1963, vol. 78, No. 2, pp. 37 to 42, 44, 45 & 48.
Aerosol Age, 12/1969, pp. 30-32, 34, 36, 38 & 69.

*Primary Examiner*—Dale R. Ore
*Attorney, Agent, or Firm*—Frank T. Barber; Carl C. Batz; Richard G. Harrer

[57] ABSTRACT

An antiperspirant composition which contains an aluminum salt, a smectite mineral and polyethyleneglycol, said composition being sprayable and in liquid form without flocculation, and the process of preparing such composition in which the aluminum salt is added to a mixture of the smectite and polyethyleneglycol.

14 Claims, No Drawings

4,338,294

ANTIPERSPIRANT COMPOSITIONS AND METHODS FOR THEIR PREPARATION

This invention relates to antiperspirant compositions and more particularly to such compositions containing an aluminum salt and smectite mineral and wherein flocculation is avoided.

BACKGROUND

Aluminum salts such as aluminum chloride ($AlCl_3.6H_2O$) or aluminum chlorhydrate ($Al(OH)_5Cl$) are known to have antiperspirant properties and have been formulated in various ways to prepare antiperspirant compositions. However, when attempts are made to use these products as lotions they cannot be applied as a mist from a manual pump and spray unit; instead the products stream and do not spread out as a mist.

It is known that smectite minerals (as defined by R. E. Grim in "Clay Mineralogy", 2nd Ed. published by McGraw-Hill Company) may be dispersed in water to produce thixotropic (i.e. sprayable) gels. Further, it is known that the smectite minerals will act as emulsion stabilizers. However, it has not been possible to incorporate these minerals into antiperspirant compositions because the smectite gels flocculate in the presence of aluminum salts.

Therefore, we have sought ways of combining the aluminum salts and smectite mineral in water so that flocculation can be avoided and a composition prepared in the form of an effective sprayable lotion, roll-on, or dab-on type of antiperspirant, and which avoids the other difficulties above mentioned.

SUMMARY

We have discovered that by including in the composition polyethyleneglycol along with the aluminum salt and smectite mineral, this avoids flocculation of the combined ingredients enabling the preparation of an antiperspirant composition to be used as an aerosol spray or a simple pump spray, a roll-on, or cream antiperspirant. A detailed explanation of my improved antiperspirant composition and the method in which it may be prepared is given in the following description.

DESCRIPTION

The aluminum salt ingredient may be any aluminum salt with a simple hydrolyzed or polymeric hydrolyzed cation. Examples are aluminum chloride ($AlCl_3$), basic aluminum chlorhydrate ($Al(OH)_5Cl$), and aluminum chlorhydratezirconylhydroxy chloride mixture. I prefer the basic aluminum salts ($Al(OH)_y \cdot X_z$ where y is 2.0 to 2.6, z is 0.4 to 1.0, $y+z=3$ and X is a halide. The amount of the aluminum salt included may vary from 1 to 50 percent, but preferably may be within the range of from 5 to 25 percent, and ideally may be about 10 percent. These percentages, and other percentages of ingredients given herein, are by weight and based on the total weight of the composition.

The smectite material may be natural or synthetic and is composed of layer silicates having the characteristic of expanding in the presence of water. Smectite is thought to be made up of units comprising two tetrahedral sheets with a central alumina octahedral sheet, and with the tips of the tetrahedrons pointing in the same direction and toward the center of the unit, and with the tetrahedral and octahedral sheets so combined so that the tetrahedrons of the silica sheet and one of the hydroxyl layers of the octahedral sheet forming a common layer. The atoms common to both the tetrahedral and octahedral layer become O instead of OH. The layers are continuous in two directions and stacked above each other in the third direction. Water may enter between the unit layers.

Especially good results are obtained when the smectite mineral employed is a synthetic layer-lattice magnesium aluminosilicate. Best results have been obtained when using a synthetic saponite such as the mineral now being sold by National Lead Company under the trademark Barasym NAS 50.

The smectite ingredient may be included in my improved composition in the amount of 0.5 to 10 percent preferably between 2.0 and 8 percent, and ideally about 5 percent.

The polyethyleneglycol ingredient may be any polyethyleneglycol having a molecular weight of from 100 to 10,000.

The amount of polyethyleneglycol to be included may be from 0.5 to 10 percent, preferably 1.5 to 8 percent and ideally about 3 percent.

The amount of water to be included may also vary and may be from 20 to 97 percent, preferably from 60 to 90 percent, and ideally about 75 percent.

The ingredients above mentioned are each essential to the improved combination. However, as stated above, this combination may for some purposes be still further improved by the inclusion of mineral oil, and when mineral oil is utilized it may be in an amount of from 0.5 to 30.0 percent, preferably from 5.0 to 10.0 percent, and ideally about 6 percent.

Other ingredients such as additional emulsifiers, color additives, and perfume may be optionally added as desired, but these form no essential part of my special combination. They may be referred to as "other additives".

In the preparation of the improved antiperspirant compositions, the smectite material may be placed in a mixer containing the water, and the mixer started so as to homogenize the smectite. Polyethyleneglycol is added and then the aluminum salt is added while continuing the agitation. The resulting mixture may then suitably be filtered through a 100 mesh screen. It is important that the polyethyleneglycol be added prior to the aluminum salt.

Should the polyethyleneglycol be added subsequent to the aluminum salt, flocculation will occur but if added before the aluminum salt, flocculation is avoided.

The oil phase ingredients, with or without the mineral oil, may be separately mixed and heated to about 70° C. The smectite-polyethyleneglycol-aluminum salt may also be heated to about this temperature and the two mixtures then put together in a combined mixture with vigorous stirring. The resulting composition may be formulated as an aerosol spray, a pump spray, a roll-on, or cream antiperspirant.

The improved composition is stable, has a satisfactory pH value (usually between 3.0 and 4.8) unflocculated and does not have any objectionable tendency to clog the nozzle when used as a spray. Surprisingly, the flocculating effect which we found to be characteristic of the aluminum salt smectite-water combination does not take place. Furthermore, and especially in the case the mineral oil is included, the improved compositions are substantially free of tackiness upon drying.

EXAMPLE 1

The following materials were utilized in the amounts stated

| Material | Amount in Percent by weight of the composition |
|---|---|
| Aluminum chlorhydrate | 9.35 |
| Polyethyleneglycol (Carbowax 600) | 2.8 |
| Smectite mineral (synthetic layer lattice magnesium aluminosilicate) | 5.6 |
| Mineral Oil | 6.23 |
| Glycerol monostearate | 0.23 |
| Perfume | 0.20 |
| Water | 75.79 |
| | 100.00 |

The smectite mineral was homogenized into water and the polyethyleneglycol mixed therein. The aluminum chlorhydrate was then stirred into the mixture and the combined mixture was filtered through a 100 mesh screen.

The oil phase ingredients, that is, the mineral oil and glycerol monostearate were separately mixed and heated to 70° C. Then the smectite mixture was heated to this same temperature and added to the heated oil phase ingredients with vigorous stirring. Then the perfume was added and stirring continued until the room temperature was reached.

This produced a low tack lotion useful as an antiperspirant pump spray.

EXAMPLE 2

The same procedure was used as set forth in Example 1 but using the following ingedients:

| Material | Percent by weight |
|---|---|
| Aluminum chlorhydrate | 10. |
| Polyethyleneglycol (Carbowax 600) | 2.8 |
| Smectite mineral (Barasym NAS50) | 5.6 |
| Mineral oil | 6.23 |
| Glycerol monostearate | 0.23 |
| Perfume | 0.20 |
| Water | 75.79 |
| | 100.00 |

This produced a low tack lotion useful particularly as an antiperspirant roll-on.

EXAMPLE 3

The following ingredients were used in the amounts stated:

| Material | Percent by weight |
|---|---|
| Aluminum chlorhydrate | 10. |
| Polyethyleneglycol (Carbowax 200) | 2. |
| Smectite mineral (Barasym NAS50) | 4. |
| Water | 84. |
| | 100.00 |

The smectite mineral was dispersed in the water and homogenized. The polyethyleneglycol and the aluminum chlorhydrate were stirred in, in the order stated.

This preparation was at room temperature throughout, otherwise the the procedure was as given in Example 1.

This produced a transparent thickened lotion.

EXAMPLE 4

The procedure of Example 3 was utilized using the following ingredients in the amounts stated:

| Material | Percent by weight |
|---|---|
| Aluminum chlorhydrate | 10. |
| Polyethyleneglycol (Carbowax 6000) | 2. |
| Smectite mineral | 4. |
| Water | 84. |
| | 100.00 |

The following Examples 5 to 10 demonstrate further variations in the preparation of our improved compositions.

EXAMPLE 5

Use the same procedure as in Example 1 except for using a very high molecular weight polyethyleneglycol (sold under the trade name Polyox WSR301) and adding this to the water phase before the addition of the aluminum chlorhydrate.

This will produce a low tack antiperspirant cream.

EXAMPLE 6

Use the same procedure as in Example 3 but with the following ingredients in the amounts stated:

| Material | Percent by weight |
|---|---|
| Aluminum chloride - 6H$_2$O | 10. |
| Polyethyleneglycol (Carbowax 6000) | 2. |
| Smectite Mineral (Barasym NAS50) | 4. |
| Water | 84. |
| | 100.00 |

EXAMPLE 7

Use the same procedure as in Example 3 but with the following ingredients:

| Material | Percent by weight |
|---|---|
| Aluminum chlorhydrate and Zirconium Hydroychloride (Al:Zr 4:1) | 5. |
| Polyethyleneglycol (Carbowax 600) | 2. |
| Smectite mineral (Barasym NAS50) | 4. |
| Water | 89. |
| | 100.00 |

EXAMPLE 8

Use the same procedure as in Example 1 but with the following ingredients:

| Material | Percent by weight |
|---|---|
| Aluminum chlorhydrate | 10. |
| Polyethyleneglycol (Carbowax 1000) | 3. |
| Montmorillonite | 4. |

-continued

| Material | Percent by weight |
|---|---|
| Mineral oil | 7. |
| Self emulsifying glycerol monostearate | .3 |
| Perfume | .2 |
| Water | 75.5 |
| | 100.00 |

The composition of the above named montmorillonite is $(OH)_4Si_8(Al_{3.34}.(M_g0.66)O_{20}(Na_{0.66})$.

EXAMPLE 9

Use the same procedure as in Example 1 with the following named ingredients.

| Material | Percent by weight |
|---|---|
| Aluminum chlorhydrate | 10. |
| Polyethyleneglycol (Carbowax 1000) | 3. |
| Hectorite | 4. |
| Isopropylpalmitate | 7. |
| Glycerol monostearate | .3 |
| Perfume | .2 |
| Water | 75.5 |
| | 100.00 |

The hectorite above listed has the composition $(OH)_4(Si_8(Mg_{5.34}Li_{0.66})O_{20}(Na_{0.66})$.

EXAMPLE 10

Use the same procedure as in Example 1 and the following listed ingredients in the amounts stated:

| Material | Percent by weight |
|---|---|
| Aluminum chlorhydrate | 10. |
| Polyethyleneglycol (Carbowax 1000) | 3. |
| Saponite | 4. |
| Hexadecylalcohol | 7. |
| Glycerol monostearate | .3 |
| Perfume | .2 |
| Water | 75.5 |
| | 100.00 |

The composition of the above named saponite is $(OH)_4(Si_{7.34}Al_{0.66})(mg_6O_{20})(Na_{0.66})$.

While I have specifically described only certain embodiments of the invention, it will be apparent to those skilled in the art that other embodiments may be practiced and many changes may be made all within the spirit of the invention and the scope of the appended claims.

I claim:

1. An antiperspirant composition comprising an aluminum salt in an amount of from 1 to 50 percent, a smectite mineral in an amount of from 0.5 to 10.0 percent, polyethylene glycol having a molecular weight of from 100 to 10,000 and in an amount of from 0.5 to 10.0 percent and water in an amount of from 20 to 97 percent, said percentages being by weight based on the total weight of the composition.

2. A composition as set forth in claim 1 in which said aluminum salt is contained in an amount of from 5.0 to 25 percent, said smectite in an amount of from 2.0 to 8.0 percent, said polyethylene glycol in an amount of from 1.5 to 8.0 percent and said water in an amount of from 20 to 97 percent.

3. A composition as set forth in claim 2 in which said aluminum salt is contained in about 10 percent, said smectite in an amount of about 5 percent, said polyethyleneglycol in an amount of about 3 percent, and said water in an amount of about 75 percent.

4. A composition as set forth in claim 1 in which said aluminum salt is basic aluminum chlorhydrate.

5. A composition as set forth in claim 1 which includes mineral oil in the amount of from 0.5 to 30 weight percent based on the total weight of the composition.

6. A composition as set forth in claim 5 in which the amount of said mineral oil is from 5.0 to 10.0 percent.

7. A composition as set forth in claim 6 in which the amount of said mineral oil is about 6 percent.

8. A composition as set forth in claim 1 in which said smectite mineral is a synthetic layer-lattice magnesium aluminosilicate.

9. A composition as set forth in claim 1 in which said smectite mineral is a synthetic saponite.

10. In a process for preparing an antiperspirant composition the step of mixing an aluminum salt with a mixture of smectite, polyethyleneglycol and water, said polyethyleneglycol having a molecular weight of from 100 to 10,000.

11. A process as set forth in claim 10 in which said salt is basic aluminum chlorhydrate.

12. A process as set forth in claim 10 in which said polyethyleneglycol is contained in the amount of from 0.5 to 10 percent and said aluminum salt in the amount of 1 to 30 percent, said percentages being by weight based on the total weight of said composition.

13. A process as set forth in claim 10 including the step of passing the resulting composition through a nozzle and into the form of a spray.

14. A process as set forth in claim 10 including the added step of mixing the resulting mixture with mineral oil.

* * * * *